United States Patent
Riebel et al.

(10) Patent No.: US 6,399,541 B1
(45) Date of Patent: Jun. 4, 2002

(54) SUBSTITUTED 2,4-DIAMINO-1,3,5-TRIAZINES AS HERBICIDES

(75) Inventors: Hans-Jochem Riebel, Wuppertal; Stefan Lehr, Langenfeld; Uwe Stelzer, Burscheid, all of (DE); Markus Dollinger, Overland Park; Hans-Joachim Santel, Leawood, both of KS (US); Peter Dahmen, Neuss (DE); Toshio Goto, Kokubunji-machi; Yukiyoshi Watanabe, Oyama, both of (JP)

(73) Assignees: Bayer Aktiengesellschaft, Leverkusen (DE); Nihon Bayer Agrochem, K.K., Tokyo (JP)

( * ) Notice: Subject to any disclaimer, the term of this patent is extended or adjusted under 35 U.S.C. 154(b) by 0 days.

(21) Appl. No.: 09/381,442
(22) PCT Filed: Mar. 9, 1998
(86) PCT No.: PCT/EP98/01362
§ 371 (c)(1),
(2), (4) Date: Oct. 18, 1999
(87) PCT Pub. No.: WO98/42684
PCT Pub. Date: Oct. 1, 1998

(30) Foreign Application Priority Data

Mar. 21, 1997 (DE) .......................................... 197 11 825

(51) Int. Cl.[7] .......................... A01N 43/68; C07D 251/18
(52) U.S. Cl. ...................... 504/234; 544/206; 504/232; 504/233
(58) Field of Search ................ 544/206; 504/232, 504/233, 234

(56) References Cited

U.S. PATENT DOCUMENTS

| | | | |
|---|---|---|---|
| 3,816,419 A | 6/1974 | Cross et al. | 260/249.9 |
| 3,932,167 A | 1/1976 | Cross et al. | 71/93 |
| 4,680,054 A | 7/1987 | Takematsu et al. | 71/93 |
| 4,844,731 A | 7/1989 | Takematsu et al. | 71/93 |
| 5,290,754 A | 3/1994 | Nishii et al. | 504/232 |
| 5,403,815 A | 4/1995 | Nishii et al. | 504/230 |

FOREIGN PATENT DOCUMENTS

JP 63-238071 10/1988

OTHER PUBLICATIONS

Ind. J. Chem, (Month Unavailable), 1963, pp. 218–220, Paul et al, "Synthesis of Biguanides as Potential Hypoglycaemic Agents: Part IV–Structure–Activity Relationship".

The Journal of the American Chemical Society, vol. 81, (Month Unavailable), 1959, pp. 3728–3736, Shapiro, etc., "Hypoglycemic Agents. III [1–3] $N^1$–Alkyl–and Aralkylbiguanides".

Primary Examiner—John M. Ford
(74) Attorney, Agent, or Firm—Joseph C. Gil

(57) ABSTRACT

The invention relates to novel substituted 2,4-diamino-1,3,5-triazines of the formula (I)

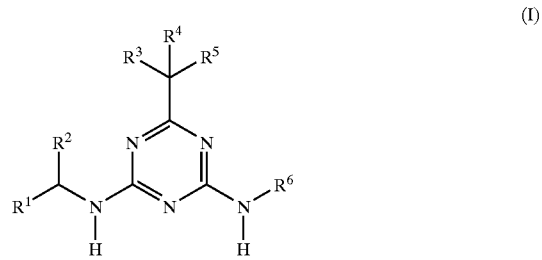

in which $R^1$ represents (in each case unsubstituted) phenyl or naphthyl $R^2$ represents alkyl, $R^3$ represents hydrogen, represents halogen or represents in each case optionally substituted alkyl, alkoxy, alkylthio, alkylsulphinyl or alkylsulphonyl, $R^4$ represents hydrogen, represents halogen or represents optionally substituted alkyl, $R^5$ represents hydrogen, represents halogen or represents optionally substituted alkyl, and $R^6$ represents hydrogen or represents in each case optionally substituted alkyl, alkylcarbonyl or alkylsulphonyl, (but where the compound 2-amino-4-(1-phenyl-ethylamino)-6-trifluoromethyl-1,3,5-triazine is excluded), to processes for preparing the novel compounds and to their use as herbicides.

14 Claims, No Drawings

SUBSTITUTED 2,4-DIAMINO-1,3,5-TRIAZINES AS HERBICIDES

This is a 371 National Application of PCT/EP98/01362, filed Mar. 9, 1998.

The invention relates to novel substituted 2,4-diamino-1,3,5-triazines, to processes for their preparation and to their use as herbicides.

A number of substituted 2,4-diamino-triazines, such as, for example, the compound 2-amino-4-(1-phenyl-ethylamino)-6-trifluoromethyl-1,3,5-triazine, are already known from the (patent) literature (cf. U.S. Pat. No. 3,816,419, cf. also U.S. Pat. No. 3,932,167, EP 191496, EP 273328, EP 411153/WO 90/09378). However, these compounds have hitherto not attained any particular importance.

This invention, accordingly, provides the novel substituted 2,4-diamino-1,3,5-triazines of the general formula (I),

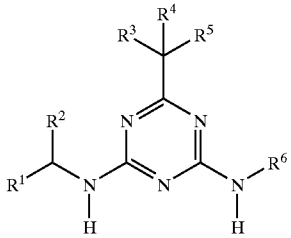

(I)

in which
- $R^1$ represents (in each case unsubstituted) phenyl or naphthyl,
- $R^2$ represents alkyl,
- $R^3$ represents hydrogen, represents halogen or represents in each case optionally substituted alkyl, alkoxy, alkylthio, alkylsulphinyl or alkylsulphonyl,
- $R^4$ represents hydrogen, represents halogen or represents optionally substituted alky,
- $R^5$ represents hydrogen, represents halogen or represents optionally substituted alkyl, and
- $R^6$ represents hydrogen or represents in each case optionally substituted alkyl, alkylcarbonyl or alkylsulphonyl, but where the known compound 2-amino-4-(1-phenyl-ethylamino)-6-trifluoromethyl-1,3,5-triazine (cf. U.S. Pat. No. 3,816,419) is excluded by disclaimer.

The novel substituted 2,4-diamino-1,3,5-triazines of the general formula (I) are obtained when (a) substituted biguanides of the general formula (II)

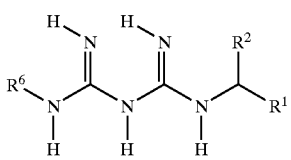

(II)

in which
$R^1$, $R^2$ and $R^6$ are each as defined above
and/or acid adducts of compounds of the general formula (II)

are reacted with alkoxycarbonyl compounds of the general formula (III)

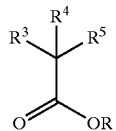

(III)

in which
$R^3$, $R^4$ and $R^5$ are each as defined above and
R represents alkyl,
if appropriate in the presence of a reaction auxiliary and if appropriate in the presence of a diluent,
or that (b) to prepare compounds of the formula (I) in which $R^6$ is different from hydrogen
2,4-diamino-1,3,5-triazines of the general formula (Ia)

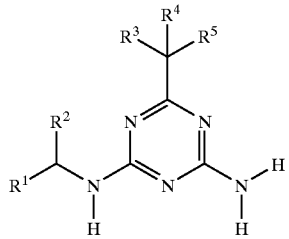

(Ia)

in which
$R^1$, $R^2$, $R^3$, $R^4$ and $R^5$ are each as defined above
are reacted with alkylating, acylating or sulphonylating agents of the general formula (IV)

$$X-R^6 \qquad (IV)$$

in which
$R^6$ is as defined above, except for hydrogen, and
X represents halogen, alkoxy, acyloxy or alkoxysulphonyloxy,
if appropriate in the presence of a reaction auxiliary and if appropriate in the presence of a diluent,
and further conversions within the scope of the above definition of substituents are carried out by customary methods, if appropriate, on the compounds of the general formula (I) obtained according to the processes described under (a) or (b).

The novel substituted 2,4-diamino-1,3,5-triazines of the general formula (I) have strong and selective herbicidal activity.

Surprisingly, the 2,4-diamino-1,3,5-triazines of the general formula (I) according to the invention exhibit considerably stronger herbicidal activity than the prior-art compound 2-amino-4-(1-phenyl-ethylamino)-6-trifluoromethyl-1,3,5-triazine, and some of them are tolerated well by crop plants, such as, for example, barley and cotton.

The compounds of the general formula (I) according to the invention contain at least one asymmetrically substituted carbon atom and can therefore be present in different enantiomeric (R- and S-configured forms) and/or diastereomeric forms. The invention relates both to the various possible individual enantiomeric or stereoisomeric forms of the compounds of the general formula (I) and to the mixtures of these isomeric compounds.

In the definitions, the hydrocarbon chains, such as alkyl, are in each case straight-chain or branched, including combination with heteroatoms, such as in alkoxy or alkylthio.

Halogen generally represents fluorine, chlorine, bromine or iodine, preferably fluorine, chlorine or bromine, in particular fluorine or chlorine.

The invention preferably provides compounds of the formula (I) in which $R^1$ represents (in each case unsubstituted) phenyl or naphthyl, $R^2$ represents alkyl having 1 to 6 carbon atoms, $R^3$ represents hydrogen, represents halogen or represents in each case optionally halogen- or $C_1$–$C_4$-alkoxy-substituted alkyl, alkoxy, alkylthio, alkylsulphinyl or alkylsulphonyl having in each case 1 to 6 carbon atoms, $R^4$ represents hydrogen, represents halogen or represents optionally halogen-substituted $C_1$–$C_6$-alkyl, $R^5$ represents hydrogen, represents halogen or represents optionally halogen-substituted $C_1$–$C_6$-alkyl, and $R^6$ represents hydrogen or represents in each case optionally halogen- or $C_1$–$C_4$-alkoxy substituted $C_1$–$C_6$-alkyl, $C_2$–$C_7$-alkylcarbonyl or $C_1$–$C_6$-alkyl-sulphonyl, but where the known compound 2-amino-4-(1-phenyl-ethylamino)-6-trifluoromethyl-1,3,5-triazine (cf. U.S. Pat. No. 3,816,419) is excluded by disclaimer.

The invention relates in particular to compounds of the formula (I) in which $R^1$ represents (in each case unsubstituted) phenyl or naphthyl, $R^2$ represents methyl, ethyl, n- or i-propyl, n-, i-, s- or t-butyl, $R^3$ represents hydrogen, represents fluorine, chlorine, bromine, or represents in each case optionally fluorine-, chlorine-, methoxy- or ethoxy-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, methylsulphonyl or ethylsulphonyl, $R^4$ represents hydrogen, represents fluorine, chlorine or bromine, or represents in each case optionally fluorine- and/or chlorine-substituted methyl, ethyl, n- or i-propyl, n-, i-, s- or t-butyl, $R^5$ represents hydrogen, represents fluorine, chlorine or bromine, or represents in each case optionally fluorine- and/or chlorine-substituted methyl, ethyl, n- or i-propyl, n-, i-, s- or t-butyl, and $R^6$ represents hydrogen or represents in each case optionally fluorine-, chlorine-, methoxy- or ethoxy-substituted methyl, ethyl, n- or i-propyl, n-, i-, s- or t-butyl, acetyl, propionyl, n- or i-butyroyl, methylsulphonyl, ethylsulphonyl, n- or i-propylsulphonyl, n-, i-, s- or t-butylsulphonyl, but where the known compound 2-amino-4-(1-phenyl-ethylamino)-6-trifluoromethyl-1,3,5-triazine (cf. U.S. Pat. No. 3,816,419) as excluded by disclaimer.

The abovementioned general or preferred radical definitions apply both to the end products of the formula (I) and, correspondingly, to the starting materials or intermediates required in each case for the preparation. These radical definitions can be combined with each other at will, i.e. including combinations between the given preferred ranges.

Using, for example, 1-(1-phenyl-propyl)-biguanide and methyl trifluoroacetate as starting materials, the course of the reaction of the process (a) according to the invention can be illustrated by the following equation:

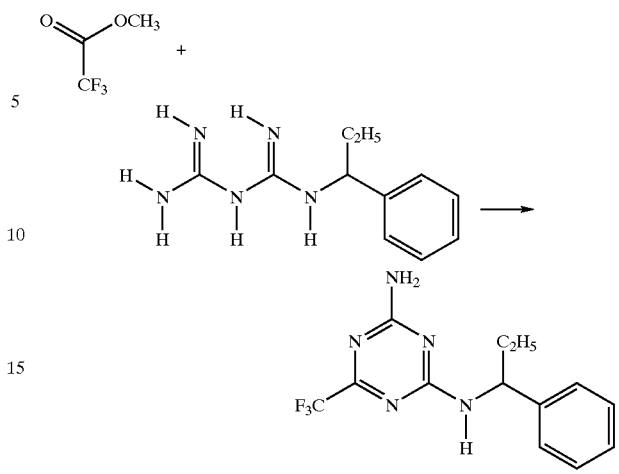

Using, for example, 2-amino-4-(2,2,2-trifluoro-1-methyl-ethyl)-6-(1-phenyl-ethyl-amino)-1,3,5-triazine and acetyl chloride as starting materials, the course of the reaction in the process (b) according to the invention can be illustrated by the following equation:

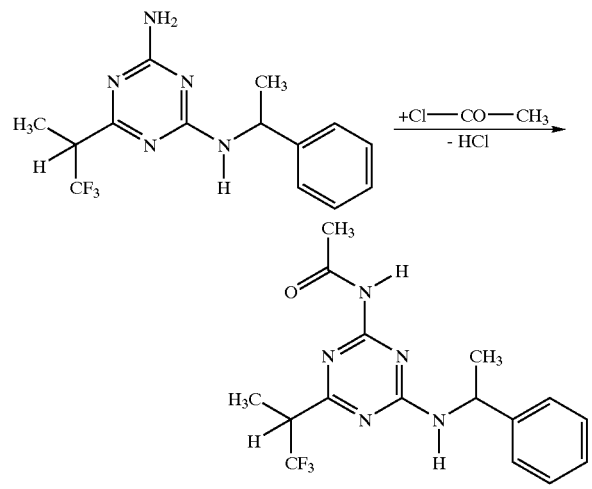

The formula (II) provides a general definition of the substituted biguanides to be used as starting materials in the process (a) according to the invention for preparing the compounds of the formula (I). In the formula (II), $R^1$, $R^2$ and $R^6$ each preferably or in particular have those meanings which have already been mentioned above in connection with the description of the compounds of the formula (I) according to the invention as being preferred or as being particularly preferred for $R^1$, $R^2$ and $R^6$.

Suitable acid adducts of compounds of the formula (I) are their addition products with protonic acids, such as, for example, with hydrogen chloride, hydrogen bromide, sulphuric acid, methanesulphonic acid, benzenesulphonic acid and p-toluene-sulphonic acid.

The starting materials of the general formula (II) are known and/or can be prepared by a process known per se (cf. U.S. Pat. No. 3,816,419; Indian J. Chem. 1 (1963), 218–220; J. Am. Chem. Soc. 81 (1959), 3728–3736).

The substituted biguanides of the general formula (II) are obtained when amines of the general formula (V)

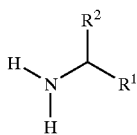

in which
R¹ and R² are each as defined above
and/or acid adducts of compounds of the general formula (V), such as, for example, the hydrochlorides are reacted with cyano guanidines of the general formula (VI)

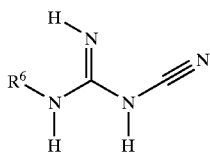

in which
R⁶ is as defined above,
if appropriate in the presence of a reaction auxiliary, such as, for example, hydrogen chloride, and if appropriate in the presence of a diluent, such as, for example, n-decane, toluene or 1,2-dichloro-benzene, at temperatures between 100° C. and 200° C. (cf. the preparation examples).

The formula (III) provides a general definition of the alkoxycarbonyl compounds further to be used as starting materials in the process (a) according to the invention for preparing compounds of the formula (I). In the formula (III), R³, R⁴ and R⁵ each preferably or in particular have those meanings which have already been mentioned above in connection with the description of the compounds of the formula (I) according to the invention as being preferred or as being particularly preferred for R³, R⁴ and R⁵; R preferably represents alkyl having 1 to 4 carbon atoms, in particular methyl or ethyl.

The starting materials of the formula (III) are known chemicals for synthesis.

The formula (Ia) provides a general definition of the 2,4-diamino-1,3,5-triazines to be used as starting materials in the process (b) according to the invention for preparing compounds of the formula (I). In the formula (Ia), R¹, R², R³, R⁴ and R⁵ each preferably or in particular have those meanings which have already been mentioned in connection with the description of the compounds of the formula (I) according to the invention as being preferred or as being particularly preferred for R¹, R², R³, R⁴ and R⁵.

The starting materials of the general formula (Ia) are, as novel compounds, also part of the subject-matter of the present application; they can be prepared according to process (a).

The formula (IV) provides a general definition of the alkylating, acylating or sulphonylating agents further to be used as starting materials in the process (b) according to the invention for preparing compounds of the formula (I). In the formula (IV), R⁶ preferably or in particular has that meaning which has already been mentioned above in connection with the description of the compounds of the formula (I) according to the invention as being preferred or as being particularly preferred for R⁶, with the exception of hydrogen; X preferably represents fluorine, chlorine, bromine, iodine, methoxy, ethoxy, acetyloxy, propionyloxy, methoxysulphonyloxy or ethoxysulphonyloxy.

The starting materials of the general formula (VI) are known chemicals for synthesis.

The processes according to the invention for preparing the compounds of the formula (I) are, if appropriate, carried out using a reaction auxiliary. Suitable reaction auxiliaries for the processes (a) and (b) are the customary inorganic or organic bases or acid acceptors. These preferably include alkali metal or alkaline earth metal acetates, amides, carbonates, bicarbonates, hydrides, hydroxides or alkoxides, such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide, ethoxide, n- or -i-propoxide, n-, i-, s- or t-butoxide or potassium methoxide, ethoxide, n- or -i-propoxide, n-, i-, s- or t-butoxide; furthermore also basic organic nitrogen compounds, such as, for example, trimethyl-amine, triethylamine, tripropylamine, tributylamine, ethyl-diisopropylamine, N,N-dimethyl-cyclohexylamine, dicyclohexylamine, ethyl-dicyclohexylamine, N,N-di-methyl-aniline, N,N-dimethyl-benzylamine, pyridine, 2-methyl-, 3-methyl-, 4-methyl-, 2,4-dimethyl-, 2,6-dimethyl-, 3,4-dimethyl- and 3,5-dimethyl-pyridine, 5-ethyl-2-methyl-pyridine, 4-dimethylamino-pyridine, N-methyl-piperidine, 1,4-diazabicyclo[2,2,2]-octane (DABCO), 1,5-diazabicyclo[4,3,0]-non-5-ene (DBN), or 1,8-diazabicyclo[5,4,0]-undec-7-ene (DBU).

Suitable diluents for carrying out the processes (a) and (b) according to the invention are, if appropriate, inert organic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl ether or ethylene glycol diethyl ether; ketones, such as methyl isopropyl ketone or methyl isobutyl ketone; nitriles, such as acetonitrile, propionitrile or butyronitrile; amides, such as N,N-dimethylformamide, N,N-dimethylacetamide, N-methyl-formanilide, N-methyl-pyrrolidone or hexamethylphosphoric triamide; esters, such as methyl acetate or ethyl acetate; sulphoxides, such as dimethyl sulphoxide, alcohols, such as methanol, ethanol, n- or i-propanol, ethylene glycol monomethyl ether, ethylene glycol monoethyl ether, diethylene glycol monomethyl ether, diethylene glycol monoethyl ether, mixtures thereof with water or pure water.

When carrying out the processes (a) and (b) according to the invention, the reaction temperatures can be varied within a relatively wide range. In general, the reactions are carried out at temperatures between 0° C. and 180° C., preferably between 10° C. and 150° C.

In general, the processes (a) and (b) according to the invention are carried out at atmospheric pressure. However, it is also possible to carry out the processes according to the invention under elevated or reduced pressure—in general between 0.1 bar and 10 bar.

To carry out the processes according to the invention, the starting materials are generally employed in approximately equimolar amounts. However, it is also possible to use one of the components in a relatively large excess. The reaction is generally carried out in a suitable diluent in the presence of a reaction auxiliary, and the reaction mixture is generally stirred for several hours at the temperature required. Work-up is carried out according to customary methods (cf. the Preparation Examples).

The active compounds according to the invention can be used as defoliants, desiccants, haulm-killers and, especially, as weed-killers. By weeds, in the broadest sense, are to be understood all plants which grow in locations where they are undesired. Whether the substances according to the invention act as total or selective herbicides depends essentially on the amount used.

The active compounds according to the invention can be used, for example, in connection with the following plants:

Dicotyledonous weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus, Taraxacum.

Dicotyledonous crops of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis, Cucurbita.

Monocotyledonous weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus, Apera.

Monocotyledonous crops of the genera: Oryza, Zea, Triticum, Hordeum, Avena, Secale, Sorghum, Panicum, Saccharum, Ananas, Asparagus, Allium.

However, the use of the active compounds according to the invention is in no way restricted to these genera, but also extends in the same manner to other plants.

The compounds are suitable, depending on the concentration, for the total control of weeds, for example on industrial terrain and rail tracks, and on paths and squares with or without tree plantings. Equally, the compounds can be employed for controlling weeds in perennial cultures, for example forests, decorative tree plantings, orchards, vineyards, citrus groves, nut orchards, banana plantations, coffee plantations, tea plantations, rubber plantations, oil palm plantations, cocoa plantations, soft fruit plantings and hopfields, on lawns, turf and pasture-land, and for the selective control of weeds in annual crops.

The compounds of the formula (I) according to the invention are particularly suitable for the selective control of monocotyledonous and dicotyledonous weeds in monocotyledonous and dicotyledonous crops by both the pre- and the post-emergence method.

The active compounds can be converted into the customary formulations, such as solutions, emulsions, wettable powders, suspensions, powders, dusting agents, pastes, soluble powders, granules, suspo-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. Suitable liquid solvents are in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethyl-formamide and dimethylsulphoxide, as well as water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates, suitable solid carriers for granules are: for example crushed and fractionated natural rocks such as calcite, marble, pumice, sepiolite, dolomite, as well as synthetic granules of inorganic and organic meals, and granules of organic material such as sawdust, coconut shells, maize cobs and tobacco stalks; suitable emulsifying and/or foam-forming agents are: for example non-ionic and anionic emulsifiers, such as polyoxyethylene fatty acid esters, polyoxyethylene fatty alcohol ethers, for example alkylaryl polyglycol ethers, alkylsulphonates, alkylsulphates, arylsulphonates as well as protein hydrolysates; suitable dispersing agents are: for example lignin-sulphite waste liquors and methylcellulose.

Tackifiers such as carboxymethylcellulose, natural and synthetic polymers in the form of powders, granules or lattices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian blue, and organic dyes, such as alizarine dyes, azo dyes and metal phthalocyanine dyes, and trace nutrients such as salts or iron, manganese, boron, copper, cobalt, molybdenum and zinc.

The formulations in general comprise between 0.1 and 95 per cent by weight of active compound, preferably between 0.5 and 90%.

For controlling weeds, the active compounds according to the invention, as such or in the form of their formulations, can also be used as mixtures with known herbicides, ready-to-use formulations or tank mixes being possible.

Possible components for the mixtures are known herbicides, for example acetochlor, acifluorfen(-sodium), aclonifen, alachlor, alloxydim(-sodium), ametryne, amidochlor, amidosulfuron, asulam, atrazine, azimsulfuron, benazolin, benfuresate, bensulfuron(-methyl), bentazon, benzofenap, benzoylprop(-ethyl), bialaphos, bifenox, bromobutide, bromofenoxim, bromoxynil, butachlor, butylate, cafenstrole, carbetamide, chlomethoxyfen, chloramben, chloridazon, chlorimuron(-ethyl), chlornitrofen, chlorsulfuron, chlortoluron, cinmethylin, cinosulfuron, clethodim, clodinafop(-propargyl), clomazone, clopyralid, clopyrasulfuron, cloransulam(-methyl), cumyluron, cyanazine, cycloate, cyclosulfamuron, cycloxydim, cyhalofop(-butyl), 2,4-D, 2,4-DB, 2,4-DP, desmedipham, diallate, dicamba, diclofop(-methyl), difenzoquat, diflufenican, dimefuron, dimepiperate, dimethachlor, dimethametryn, dimethenamid, dinitramine, diphenamid, diquat, dithiopyr, diuron, dymron, EPTC, esprocarb, ethalfluralin, ethametsulfuron(-methyl), ethofumesate, ethoxyfen, etobenzanid, fenoxaprop(-ethyl), flamprop(-isopropyl), flamprop(-isopropyl-L), flamprop(-methyl), flazasulfuron, fluazifop(-butyl), flumetsulam, flumiclorac(-pentyl), flumioxazin, flumipropyn, fluometuron, fluorochloridone, fluoroglycofen(-ethyl), flupoxam, flupropacil, flurenol, fluridone, fluroxypyr, flurprimidol, flurtamone, fluthiamide, fomesafen, glufosinate(-ammonium), glyphosate(-isopropylammonium), halosafen, haloxyfop(-ethoxyethyl), hexazinone, imazamethabenz(-methyl), imazamethapyr, imazamox, imazapyr, imazaquin, imazethapyr, imazosulfuron, ioxynil, isopropalin, isoproturon, isoxaben, isoxaflutole, isoxapyrifop, lactofen, lenacil, linuron, MCPA, MCPP, mefenacet, metamitron, metazachlor, methabenzthiazuron, metobenzuron, metobromuron, metolachlor, metosulam, metoxuron, metribuzin, metsulfuron(-methyl), molinate, monolinuron, naproanilide, napropamide, neburon, nicosulfuron, norflurazon orbencarb, oryzalin, oxadiazon, oxyfluorfen, paraquat, pendimethalin, phenmedipham, piperophos, pretilachlor, primisulfuron(-methyl), prometryn, propachlor, propanil, propaquizafop, propyzamide, prosulfocarb, prosulfuron, pyrazolate, pyrazosulfuron(-ethyl), pyrazoxyfen, pyributicarb, pyridate, pyrithiobac(-sodium), quinchlorac, quinmerac, quizalofop(-ethyl), quizalofop(-p-tefuryl), rimsulfuron, sethoxydim, simazine, simetryn, sulcotrione, sulfentrazone, sulfometuron(-methyl), sulfosate, tebutam, tebuthiuron, terbuthylazine, terbutryn, thenylchlor, thiazopyr, thidiazimin, thifensulfuron(-methyl), thiobencarb, tiocarbazil, tralkoxydim, triallate, triasulfuron, tribenuron(-methyl), triclopyr, tridiphane, trifluralin and triflusulfuron.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 1 g and 10 kg of active compound per hectare of soil surface, preferably between 5 g and 5 kg per ha.

The preparation and use of the active compounds according to the invention can be seen from the examples below.

PREPARATION EXAMPLES

EXAMPLE 1

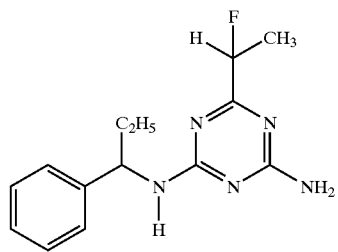

(Process (a))

At 20° C., a solution of 3.5 g (65 mmol) of sodium methoxide in 15 ml of methanol is added dropwise with stirring to a mixture of 15.5 g (60 mmol) of 1-(1-phenyl-propyl)-biguanide (racemic), 8.0 g (60 mmol) of ethyl 2-fluoro-propanoate and 100 ml of methanol, and the reaction mixture is then stirred for 15 hours at room temperature (about 20° C.). The mixture is then shaken with methylene chloride and water, and the organic phase is separated off, washed with 1N aqueous sodium hydroxide solution, dried with sodium sulphate and filtered. The solvent is carefully distilled off from the filtrate under water pump vacuum.

This gives 13 g (78% of theory) of 2-amino-4-(1-fluoro-ethyl)-6-(1-phenyl-propyl-amino)-1,3,5-triazine (racemate) as an amorphous residue.

EXAMPLE 2

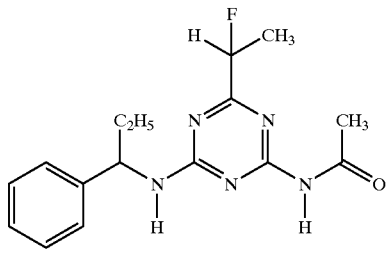

(Process (b))

At 130° C., a mixture of 10 g (36 mmol) of 2-amino-4-(1-fluoro-ethyl)-6-(1-phenyl-propylamino)-1,3,5-triazine (racemic) and 70 ml of acetic anhydride is stirred for 2 hours and, after cooling to room temperature (about 20° C.), stirred with 150 ml of water and 150 ml of methylene chloride. The organic phase is then separated off, dried with sodium sulphate and filtered. The filtrate is concentrated under water pump vacuum, the residue is digested with a little ethanol and the resulting crystalline product is isolated by filtration with suction.

This gives 2.2 g (19% of theory) of 2-acetylamino-4-(1-fluoro-ethyl)-6-(1-phenyl-propylamino)-1,3,5-triazine (racemate) of melting point 118° C.

By the methods of Preparation Examples 1 and 2, and in accordance with the general description of the preparation process according to the invention, it is also possible to prepare, for example, the compounds of the formula (I) listed in Table 1 below.

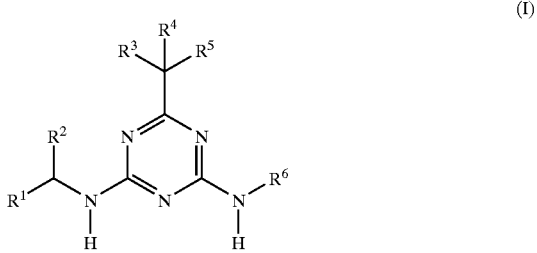

TABLE 1

Examples of compounds of the formula (I)

| Ex. No. | R¹ | R² | R³ | R⁴ | R⁵ | R⁶ | Physical data |
|---|---|---|---|---|---|---|---|
| 3 | phenyl | $C_2H_5$ | F | F | F | H | (amorphous) (racemate) |
| 4 | phenyl | $C_2H_5$ | F | F | F | $COCH_3$ | m.p.: 112° C. (racemate) |
| 5 | phenyl | $C_3H_7$-i | F | F | F | H | (amorphous) (racemate) |
| 6 | phenyl | $C_3H_7$-i | F | F | F | $COCH_3$ | m.p. 134° C. (racemate) |
| 7 | phenyl | $C_2H_5$ | $CH_3$ | $CH_3$ | F | H | (amorphous) (racemate) |
| 8 | phenyl | $C_2H_5$ | $CH_3$ | $CH_3$ | F | $COCH_3$ | m.p. 117° C. (racemate) |
| 9 | phenyl | $C_3H_7$-i | $CH_3$ | F | H | H | (amorphous) (racemate) |
| 10 | phenyl | $C_3H_7$-i | $CH_3$ | $CH_3$ | F | H | (amorphous) (racemate) |
| 11 | phenyl | $C_3H_7$-i | $CH_3$ | F | H | $COCH_3$ | m.p.: 98° C. (racemate) |
| 12 | phenyl | $C_3H_7$-i | $CH_3$ | $CH_3$ | F | $COCH_3$ | m.p.: 124° C. (racemate) |
| 13 | phenyl | $CH_3$ | $CH_3$ | $CH_3$ | F | H | $n_D^{20}$ = 1.5513 (racemate) |
| 14 | phenyl | $CH_3$ | $CH_3$ | $CH_3$ | F | H | $n_D^{20}$ = 1.5388 (R enantiomer) |
| 15 | phenyl | $CH_3$ | $CH_3$ | $CH_3$ | F | H | $n_D^{20}$ = 1.5450 (S enantiomer) |

TABLE 1-continued

Examples of compounds of the formula (I)

| Ex. No. | R¹ | R² | R³ | R⁴ | R⁵ | R⁶ | Physical data |
|---|---|---|---|---|---|---|---|
| 16 | 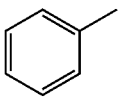 | CH₃ | CH₃ | F | H | H | $n_D^{20}$ = 1.5472 (racemate) |
| 17 | 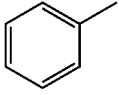 | CH₃ | CH₃ | F | H | H | $n_D^{20}$ = 1.5430 (S enantiomer) |
| 18 | 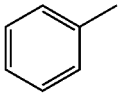 | CH₃ | CH₃ | Cl | H | H | $n_D^{20}$ = 1.5920 (racemate) |
| 19 | 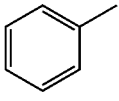 | CH₃ | CH₃ | Br | H | H | $n_D^{20}$ = 1.5715 (racemate) |
| 20 | 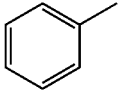 | CH₃ | CH₃ | CH₃ | Br | H | $n_D^{20}$ = 1.5673 (racemate) |
| 21 | 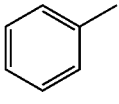 | CH₃ | CH₃ | CH₃ | CH₃ | H | $n_D^{20}$ = 1.5572 (racemate) |
| 22 | 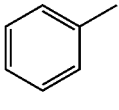 | CH₃ | C₂H₅ | H | H | H | $n_D^{20}$ = 1.5640 (racemate) |
| 23 | 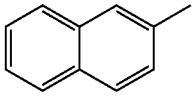 | CH₃ | F | F | F | H | (amorphous) (racemate) |
| 24 | 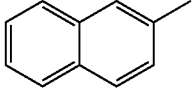 | CH₃ | F | F | F | H | (amorphous) (R enantiomer) |
| 25 | 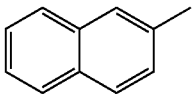 | CH₃ | F | F | F | COCH₃ | m.p.: 136° C. (S enantiomer) |
| 26 | 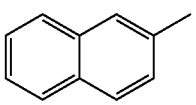 | CH₃ | F | F | F | COCH₃ | m.p.: 136° C. (R enantiomer) |
| 27 | 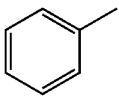 | C₂H₅ | F | F | F | H | $[\alpha]_D^{20}$ = −78° (S enantiomer) |
| 28 | 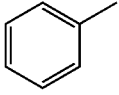 | C₂H₅ | CH₃ | F | H | H | $[\alpha]_D^{20}$ = −80° (S enantiomer) |

TABLE 1-continued

Examples of compounds of the formula (I)

| Ex. No. | R¹ | R² | R³ | R⁴ | R⁵ | R⁶ | Physical data |
|---|---|---|---|---|---|---|---|
| 29 | phenyl | $C_2H_5$ | $CH_3$ | $CH_3$ | F | H | $[\alpha]_D^{20} = -71°$ (S enantiomer) |
| 30 | phenyl | $C_2H_5$ | $CH_3$ | H | H | H | $[\alpha]_D^{20} = -80°$ (S enantiomer) |
| 31 | phenyl | $C_2H_5$ | $CH_3$ | Cl | H | H | $[\alpha]_D^{20} = -76°$ (S enantiomer) |
| 32 | phenyl | $C_2H_5$ | Cl | Cl | H | H | $[\alpha]_D^{20} = -81°$ (S enantiomer) |
| 33 | phenyl | $C_2H_5$ | F | F | F | $COCH_3$ | $[\alpha]_D^{20} = -69°$ (S enantiomer) |
| 34 | phenyl | $C_2H_5$ | $CH_3$ | F | H | $COCH_3$ | $[\alpha]_D^{20} = -57°$ (S enantiomer) |
| 35 | phenyl | $C_2H_5$ | $CH_3$ | $CH_3$ | F | $COCH_3$ | $[\alpha]_D^{20} = -53°$ (S enantiomer) |
| 36 | phenyl | $C_2H_5$ | $CH_3$ | H | H | $COCH_3$ | $[\alpha]_D^{20} = -56°$ (S enantiomer) |
| 37 | phenyl | $C_2H_5$ | $CH_3$ | Cl | H | $COCH_3$ | $[\alpha]_D^{20} = -64°$ (S enantiomer) |
| 38 | phenyl | $C_2H_5$ | Cl | Cl | H | $COCH_3$ | $[\alpha]_D^{20} = -65°$ (S enantiomer) |
| 39 | phenyl | $C_2H_5$ | $CH_3$ | F | H | H | $[\alpha]_D^{20} = +118.5°$ (R enantiomer) |
| 40 | naphthyl | $C_2H_5$ | $CH_3$ | F | H | H | (amorphous) (racemate) |
| 41 | naphthyl | $C_2H_5$ | $CH_3$ | $CH_3$ | F | H | (amorphous) (racemate) |

TABLE 1-continued

Examples of compounds of the formula (I)

| Ex. No. | R¹ | R² | R³ | R⁴ | R⁵ | R⁶ | Physical data |
|---|---|---|---|---|---|---|---|
| 42 | phenyl | $C_3H_7$-i | $CH_3$ | F | H | $COCH_3$ | (amorphous) (R enantiomer) |
| 43 | phenyl | $C_3H_7$-i | $CH_3$ | F | H | $COCH_3$ | (amorphous) (S enantiomer) |
| 44 | phenyl | $C_3H_7$-i | $CH_3$ | $CH_3$ | F | $COCH_3$ | (amorphous) (R enantiomer) |
| 45 | phenyl | $C_3H_7$-i | $CH_3$ | $CH_3$ | F | $COCH_3$ | (amorphous) (S enantiomer) |
| 46 | phenyl | $C_2H_5$ | $CH_3$ | $CH_3$ | F | H | $[\alpha]_D^{20} = +80.0°$ (R enantiomer) |
| 47 | phenyl | $C_3H_7$-i | $CH_3$ | F | H | H | (amorphous) (R enantiomer) |
| 48 | phenyl | $C_3H_7$-i | $CH_3$ | F | H | H | (amorphous) (S enantiomer) |
| 49 | phenyl | $C_3H_7$-i | $CH_3$ | $CH_3$ | F | H | (amorphous) (R enantiomer) |
| 50 | phenyl | $C_3H_7$-i | $CH_3$ | $CH_3$ | F | H | (amorphous) (R-Enantiomer) |
| 51 | phenyl | $C_2H_5$ | F | F | F | H | $[\alpha]_D^{20} = +103.5°$ (R enantiomer) |
| 52 | phenyl | $C_2H_5$ | $CH_3$ | H | H | H | $[\alpha]_D^{20} = +98.9°$ (R enantiomer) |
| 53 | phenyl | $C_2H_5$ | $CH_3$ | Cl | H | H | $[\alpha]_D^{20} = +89.0°$ (R enantiomer) |
| 54 | phenyl | $C_2H_5$ | Cl | Cl | H | H | $[\alpha]_D^{20} = +86.1°$ (R enantiomer) |

TABLE 1-continued

Examples of compounds of the formula (I)

| Ex. No. | R¹ | R² | R³ | R⁴ | R⁵ | R⁶ | Physical data |
|---|---|---|---|---|---|---|---|
| 55 | phenyl | $C_2H_5$ | F | F | F | $COCH_3$ | $[\alpha]_D^{20} = +72.2°$ (R enantiomer) |
| 56 | phenyl | $C_2H_5$ | $CH_3$ | F | H | $COCH_3$ | $[\alpha]_D^{20} = +91.5°$ (R enantiomer) |
| 57 | phenyl | $C_2H_5$ | $CH_3$ | $CH_3$ | F | $COCH_3$ | $[\alpha]_D^{20} = 65.2°$ (R enantiomer) |
| 58 | phenyl | $C_2H_5$ | $CH_3$ | H | H | $COCH_3$ | $[\alpha]_D^{20} = +70.0°$ (R enantiomer) |
| 59 | phenyl | $C_2H_5$ | $CH_3$ | Cl | H | $COCH_3$ | $[\alpha]_D^{20} = +76.4°$ (R enantiomer) |
| 60 | phenyl | $C_2H_5$ | Cl | Cl | H | $COCH_3$ | $[\alpha]_D^{20} = +75.7°$ (R enantiomer) |
| 61 | naphthyl | $CH_3$ | $OCH_3$ | H | H | H | m.p.: 85° C. (racemate) |
| 62 | naphthyl | $C_2H_5$ | $CH_3$ | H | H | H | m.p.: 70° C. (racemate) |
| 63 | naphthyl | $C_2H_5$ | $CH_3$ | Cl | H | H | m.p.: 60° C. (racemate) |
| 64 | phenyl | $C_2H_5$ | $CH_3$ | Br | H | H | (amorphous) (racemate) |
| 65 | phenyl | $C_3H_7$-n | $CH_3$ | F | H | H | (amorphous) (racemate) |
| 66 | phenyl | $C_3H_7$-n | $CH_3$ | $CH_3$ | F | H | (amorphous) (racemate) |
| 67 | phenyl | $CH_3$ | $CH_3$ | $CH_3$ | F | $COCH_3$ | (amorphous) (S enantiomer) |

TABLE 1-continued

Examples of compounds of the formula (I)

| Ex. No. | R¹ | R² | R³ | R⁴ | R⁵ | R⁶ | Physical data |
|---|---|---|---|---|---|---|---|
| 68 | phenyl | CH$_3$ | CH$_3$ | CH$_3$ | F | COC$_2$H$_5$ | (amorphous) (S enantiomer) |
| 69 | phenyl | CH$_3$ | CH$_3$ | CH$_3$ | H | H | $n_D^{20}$ = 1.5649 (racemate) |
| 70 | phenyl | CH$_3$ | CF$_3$ | F | F | H | $n_D^{20}$ = 1.5084 (racemate) |
| 71 | phenyl | CH$_3$ | CH$_2$OCH$_3$ | H | H | H | $n_D^{20}$ = 1.5683 (racemate) |
| 72 | phenyl | CH$_3$ | F | H | H | H | m.p.: 166° C. (racemate) |
| 73 | phenyl | CH$_3$ | H | H | H | H | (amorphous) (S enantiomer) |
| 74 | phenyl | CH$_3$ | CH$_3$ | H | H | H | (amorphous) (S enantiomer) |
| 75 | phenyl | CH$_3$ | OCH$_3$ | H | H | H | (amorphous) (S enantiomer) |
| 76 | phenyl | CH$_3$ | Cl | Cl | H | H | (amorphous) (S enantiomer) |
| 77 | phenyl | C$_3$H$_7$-n | CH$_3$ | F | H | COC$_2$H$_5$ | $n_D^{20}$ = 1.5416 (racemate) |
| 78 | phenyl | C$_3$H$_7$-n | CH$_3$ | CH$_3$ | F | COC$_2$H$_5$ | $n_D^{20}$ = 1.5399 (racemate) |
| 79 | phenyl | C$_2$H$_5$ | CH$_3$ | F | H | COC$_2$H$_5$ | $[\alpha]_D^{20}$ = −66.02° (S enantiomer) |
| 80 | phenyl | C$_2$H$_5$ | CH$_3$ | F | H | COC$_3$H$_7$-n | $[\alpha]_D^{20}$ = −64.25° (S enantiomer) |

TABLE 1-continued

Examples of compounds of the formula (I)

| Ex. No. | R¹ | R² | R³ | R⁴ | R⁵ | R⁶ | Physical data |
|---|---|---|---|---|---|---|---|
| 81 | phenyl | $C_2H_5$ | $CH_3$ | F | H | $COCH(CH_3)_2$ | $[\alpha]_D^{20} = -61.03°$ (S enantiomer) |
| 82 | phenyl | $C_2H_5$ | $CH_3$ | F | H | $COCH_2CH(CH_3)_2$ | $[\alpha]_D^{20} = -60.96°$ (S enantiomer) |

Starting Materials of the Formula (II)

EXAMPLE (II-1)

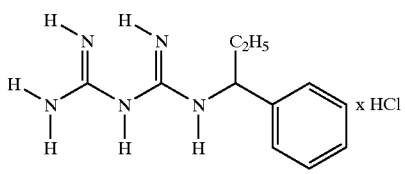

A mixture of 27 g (0.21 mol) of 1-phenyl-ethylamine (racemic), 22 ml of 33% strength aqueous hydrochloric acid and about the same amount of toluene is concentrated to dryness under water pump vacuum. 17 g (0.21 mol) of dicyanodiamide (cyanoguanidine) are added to the residue, and the mixture is then heated at 150° C. for two hours, giving a melt.

The resulting crude product—1-(1-phenyl-propyl)-biguanide hydrochloride (racemic)—is employed directly for preparing compounds of the formula (I).

By the method of Example (II-1) it is also possible to prepare, for example, the compounds of the formula (II) listed in Table 2 below or hydrochlorides thereof.

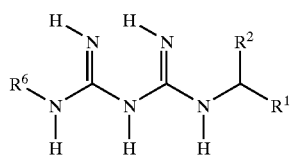
(II)

TABLE 2

Examples of compounds of the formula (II)

| Ex. No. | R¹ | R² | R⁶ | Melting point (° C.) |
|---|---|---|---|---|
| II-2 | phenyl | $C_3H_7$-i | H | 190 (hydrochloride) (racemate) |
| II-3 | phenyl | $CH_3$ | H | (amorphous) (hydrochloride) (racemate) |
| II-4 | phenyl | $C_3H_7$-n | H | (amorphous) (hydrochloride) (racemate) |
| II-5 | phenyl | $C_2H_5$ | H | (amorphous) (hydrochloride) (S enantiomer) |
| II-6 | phenyl | $C_2H_5$ | H | (amorphous) (hydrochloride) (R enantiomer) |
| II-7 | phenyl | $CH_3$ | H | (amorphous) (hydrochloride) (R enantiomer) |

USE EXAMPLES

The known compound (A) is used as comparative substance in the use examples below:

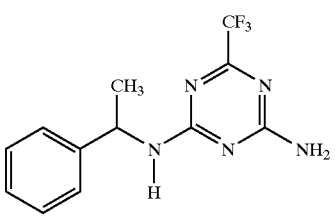
(A)

2-Amino-4-(1-phenyl-ethylamino)-6-trifluoromethyl-1,3,5-triazine (cf. U.S. Pat. No. 3,816,419)

EXAMPLE A

Pre-emergence Test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After about 24 hours, the soil is sprayed with the preparation of active compound in such a way that the particular amounts of active compound desired are employed per unit area. The concentration of the spray liquor is chosen such that the particular amounts of active compound desired are applied in 1000 l of water/ha.

After three weeks, the degree of damage to the plants is assessed in % damage in comparison to the development of the untreated control.

The figures denote:

0%=no effect (as untreated control) 100%=total destruction

In this test, for example, the compounds of Preparation Example 1, 2, 13, 14, 15, 16, 17 and 18 exhibit considerably strong action against weeds than the known compound (A) -cf. Table A -, and some of them are tolerated well by crop plants, such as, for example, cotton, barley and rapeseed. "ai"="active ingredient"

TABLE A

Pre-emergence test/greenhouse

| Active compound of preparation Ex. No. | Application rate (g of ai./ha) | Alopecurus | Avena fatua | Abutilon | Amaranthus | Galium | Xanthium |
|---|---|---|---|---|---|---|---|
| (A) | 1000 | 30 | 0 | 0 | 70 | 60 | 70 |
| (1) | 1000 | 100 | 70 | 70 | 100 | 100 | 100 |

| Active compound of preparation Ex. No. | Application rate (g of ai./ha) | Alopecurus | Setaria | Abutilon | Amaranthus |
|---|---|---|---|---|---|
| (A) | 1000 | 30 | 20 | 0 | 70 |
| (2) | 1000 | 90 | 70 | 100 | 100 |

| Active compound of preparation Ex. No. | Application rate (g of ai./ha) | Reapseed | Amaranthus | Chenopodium | Datura | Matricaria | Solanum |
|---|---|---|---|---|---|---|---|

TABLE A-continued
Pre-emergence test/greenhouse
| Structure | Rate | | | | | | |
|---|---|---|---|---|---|---|---|
| 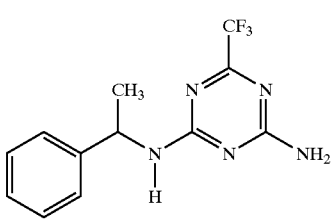 (A) | 125 | 40 | 40 | 20 | 0 | 0 | 0 |
| 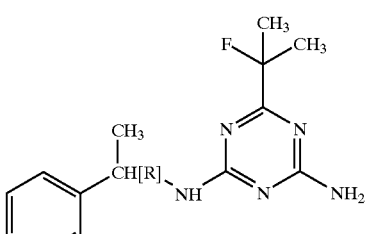 (14) | 125 | 0 | 100 | 100 | 95 | 95 | 95 |
| Active compound of preparation Ex. No. | Application rate (g of ai./ha) | Barley | Cotton | Veronica | Viola |
|---|---|---|---|---|---|
| 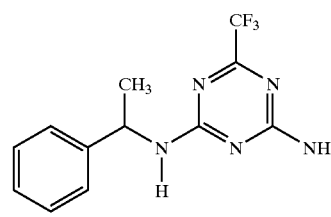 (A) | 250 | 0 | 0 | 20 | 0 |
| 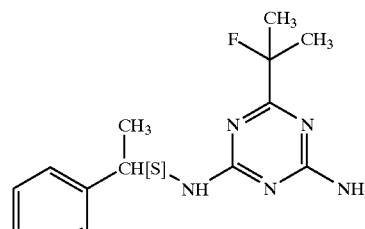 (15) | 250 | 0 | 0 | 100 | 100 |
| Active compound of preparation Ex. No. | Application rate (g of ai./ha) | Alopecurus | Avena fatua | Abutilon | Amaranthus | Veronica | Viola |
|---|---|---|---|---|---|---|---|
| 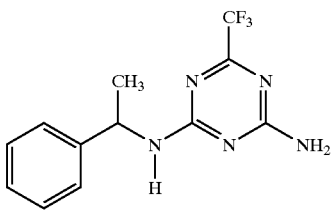 (A) | 250 | 30 | 0 | 0 | 80 | 20 | 0 |

TABLE A-continued

Pre-emergence test/greenhouse

| Structure | Application rate (g of ai./ha) | | | | | | |
|---|---|---|---|---|---|---|---|
| (17) 2-[CH(F)(CH3)]-4-NH-CH(CH3)(Ph)[S]-6-NH2-triazine | 250 | 80 | 80 | 80 | 95 | 100 | 95 |

| Active compound of preparation Ex. No. | Application rate (g of ai./ha) | Alopecurus | Avena fatua | Setaria | Cassia | Ipomoea | Viola |
|---|---|---|---|---|---|---|---|
| (A) 2-CF3-4-NH-CH(CH3)(Ph)-6-NH2-triazine | 250 | 30 | 0 | 0 | 20 | 20 | 0 |
| (13) 2-C(F)(CH3)2-4-NH-CH(CH3)(Ph)-6-NH2-triazine | 250 | 90 | 90 | 80 | 100 | 80 | 100 |

| Active compound of preparation Ex. No. | Application rate (g of ai./ha) | Alopecurus | Lolium | Sorghum | Abutilon | Amaranthus | Cassia | Ipomoea |
|---|---|---|---|---|---|---|---|---|
| (A) 2-CF3-4-NH-CH(CH3)(Ph)-6-NH2-triazine | 250 | 30 | 0 | 0 | 0 | 80 | 20 | 20 |
| (16) 2-[CH(F)(CH3)]-4-NH-CH(CH3)(Ph)-6-NH2-triazine | 250 | 100 | 100 | 95 | 80 | 100 | 100 | 100 |

| Active compound of preparation Ex. No. | Application rate (g of ai./ha) | Reapseed | Amaranthus | Ipomoea |
|---|---|---|---|---|

TABLE A-continued

Pre-emergence test/greenhouse

| Compound | | | | |
|---|---|---|---|---|
| (A) [structure: phenyl-CH(CH3)-NH-triazine(CF3)(NH2)] | 250 | 40 | 80 | 20 |
| (18) [structure: phenyl-CH(CH3)-NH-triazine-C(Cl)(CH3)H with NH2] | 250 | 0 | 100 | 95 |

EXAMPLE B

Post-emergence Test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Test plants which have a height of 5 to 15 cm are sprayed with the preparation of active compound in such a way that the particular amounts of active compound desired are applied per unit area. The concentration of the spray liquor is chosen such that the particular amounts of active compound desired are applied in 1000 l of water/ha.

After three weeks, the degree of damage to the plants is assessed in % damage in comparison to the development of the untreated control.

The figures denote:

0%=no effect (as untreated control)

100%=total destruction

In this test, for example, the compounds of Preparation Example 1, 2, 13 and 18 exhibit considerably stronger activity against weeds than the known compound (A) -cf. Table B -, and some of them are tolerated well by crop plants, such as, for example, wheat and barley.

TABLE B

Post-emergence test/greenhouse

| Active compound of preparation Ex. No. | Application rate (g of ai./ha) | Cassia | Ipomoea | Matricaria | Veronica |
|---|---|---|---|---|---|
| (A) [structure: phenyl-CH(CH3)-NH-triazine(CF3)(NH2)] | 125 | 80 | 90 | 60 | 90 |

TABLE B-continued

Post-emergence test/greenhouse

| Active compound of preparation Ex. No. | Application rate (g of ai./ha) | | | | |
|---|---|---|---|---|---|
| Compound (1): phenyl-CH(C2H5)-NH-[triazine-CH(F)(CH3)]-NH2 | 125 | 90 | 100 | 80 | 100 |

| Active compound of preparation Ex. No. | Application rate (g of ai./ha) | Ipomoea | Polygonum | Solanum | Veronica |
|---|---|---|---|---|---|
| Compound (A): phenyl-CH(CH3)-NH-[triazine-CF3]-NH2 | 60 | 80 | 80 | 40 | 70 |
| Compound (1): phenyl-CH(C2H5)-NH-[triazine-CH(F)(CH3)]-NH2 | 60 | 100 | 100 | 95 | 95 |

| Active compound of preparation Ex. No. | Application rate (g of ai./ha) | Echinochloa | Setaria | Cassia | Ipomoea | Matricaria | Veronica | Xanthium |
|---|---|---|---|---|---|---|---|---|
| Compound (A): phenyl-CH(CH3)-NH-[triazine-CF3]-NH2 | 125 | 50 | 50 | 80 | 90 | 60 | 90 | 60 |
| Compound (2): phenyl-CH(C2H5)-NH-[triazine-CH(F)(CH3)]-NH-C(O)CH3 | 125 | 80 | 80 | 100 | 100 | 95 | 95 | 80 |

| Active compound of preparation Ex. No. | Application rate (g of ai./ha) | Wheat | Cassia | Solanum | Veronica |
|---|---|---|---|---|---|

TABLE B-continued

Post-emergence test/greenhouse

| Structure | | | | | |
|---|---|---|---|---|---|
| (A) CF₃-triazine with NHCH(CH₃)Ph and NH₂ | 60 | 0 | 40 | 40 | 70 |
| (18) C(Cl)(CH₃)₂-triazine with NHCH(CH₃)Ph and NH₂ | 60 | 0 | 70 | 90 | 95 |

| Active compound of preparation Ex. No. | Application rate (g of ai./ha) | Barley | Wheat | Cassia | Ipomoea | Veronica |
|---|---|---|---|---|---|---|
| (A) CF₃-triazine with NHCH(CH₃)Ph and NH₂ | 125 | 5 | 0 | 80 | 90 | 90 |
| (13) C(F)(CH₃)₂-triazine with NHCH(CH₃)Ph and NH₂ | 125 | 0 | 0 | 95 | 100 | 100 |

What is claimed is:

1. A compound of the formula (I)

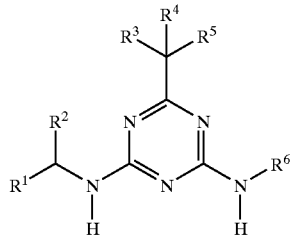

(I)

wherein
R¹ represents unsubstituted phenyl,
R² represents alkyl having 1 to 6 carbon atoms,
$R^3$ represents unsubstituted, fluoro- or methoxy-substituted methyl or unsubstituted ethyl,
$R^4$ represents hydrogen or methyl,
$R^5$ represents fluorine, and
$R^6$ represents hydrogen or represents unsubstituted or halogen- or $C_1$–$C_4$-alkoxy substituted $C_1$–$C_6$-alkyl, $C_2$–$C_7$-alkylcarbonyl or $C_1$–$C_6$-alkylsulphonyl.

2. A compound of the formula (I) according to claim 1, wherein
$R^1$ represents unsubstituted phenyl,
$R^2$ represents alkyl having 1 to 6 carbon atoms,
$R^3$ represents unsubstituted, fluoro- or methoxy-substituted methyl or unsubstituted ethyl,
$R^4$ represents hydrogen or methyl,
$R^5$ represents fluorine, and
$R^6$ represents hydrogen or represents in each case unsubstituted or halogen- or $C_1$–$C_4$-alkoxy substituted $C_1$–$C_6$-alkyl or $C_2$–$C_7$-alkyl-carbonyl.

3. A compound of the formula (I) according to claim 1, wherein
$R^1$ represents unsubstituted phenyl,
$R^2$ represents methyl, ethyl, n- or i-propyl, n-, i-, s- or t-butyl,
$R^3$ represents unsubstituted, fluoro- or methoxy-substituted methyl or unsubstituted ethyl,
$R^4$ represents hydrogen,
$R^5$ represents fluorine, and
$R^6$ represents hydrogen or represents in each case optionally fluorine-, chlorine-, methoxy- or ethoxy-substituted methyl, ethyl, n- or i-propyl, n-, i-, s- or t-butyl, acetyl, propionyl, n- or i-butyroyl, methylsulphonyl, ethylsulphonyl, n- or i-propylsulphonyl, n-, i-, s- or t-butylsulphonyl.

4. A herbicidal composition comprising one or more compounds of the formula (I) according to claim 1 and extenders and/or surfactants.

5. A method for controlling weeds and/or undesirable vegetation comprising applying an effective amount of one or more compounds of the formula (I) according to claim 1 to the weeds or their habitat.

6. A compound of the formula (I) according to claim 1, wherein $R^6$ represents halogen- or $C_1$–$C_4$-alkoxy substituted $C_1$–$C_6$-alkyl or represents unsubstituted or halogen- or $C_1$–$C_4$-alkoxy substituted $C_2$–$C_7$-alkyl-carbonyl or $C_1$–$C_6$-alkylsulphonyl.

7. A compound of the formula (I) according to claim 1, wherein $R^3$ represents unsubstituted, fluoro- or methoxy-substituted methyl.

8. A compound of the formula (I)

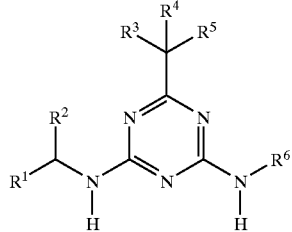

(I)

wherein
$R^1$ represents unsubstituted phenyl,
$R^2$ represents ethyl, n- or i-propyl, n-, i-, s- or t-butyl,
$R^3$ represents unsubstituted, fluoro- or methoxy-substituted methyl or unsubstituted ethyl,
$R^4$ represents hydrogen or methyl,
$R^5$ represents fluorine, and
$R^6$ represents hydrogen or represents unsubstituted or halogen- or $C_1$–$C_4$-alkoxy substituted $C_1$–$C_6$-alkyl, $C_2$–$C_7$-alkylcarbonyl or $C_1$–$C_6$-alkylsulphonyl.

9. A compound of the formula (I) according to claim 1, wherein when $R^2$ represents methyl then $R^6$ is other than hydrogen.

10. A compound of the formula (I) according to claim 1, wherein when $R^2$ represents methyl then $R^6$ represents unsubstituted or fluorine-, chlorine methoxy- or ethoxy-substituted methyl, ethyl, n- or i-propyl, n-, i-, s- or t-butyl, acetyl, propionyl, n- or i-butyroyl, methylsulphonyl, ethylsulphonyl, n- or i-propylsulphonyl, n-, i-, s- or t-butylsulphonyl.

11. A compound of the formula (I) according to claim 1, wherein
$R^3$ represents methyl,
$R^4$ represents hydrogen, and
$R^5$ represents fluorine.

12. A compound of the formula (I) according to claim 13, wherein
$R^3$ represents methyl,
$R^4$ represents hydrogen, and
$R^5$ represents fluorine.

13. A compound of the formula (I)

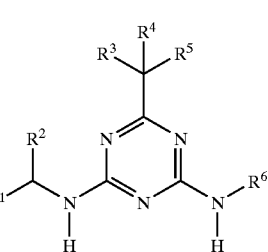

(I)

wherein
$R^1$ represents unsubstituted phenyl,
$R^2$ represents ethyl, n- or i-propyl, n-, i-, s- or t-butyl,
$R^3$ represents unsubstituted or halogen- or $C_1$–$C_4$-alkoxy-substituted alkyl having 1 to 6 carbon atoms,
$R^4$ represents hydrogen or represents unsubstituted $C_1$–$C_6$-alkyl,
$R^5$ represents halogen, and
$R^6$ represents unsubstituted or $C_1$–$C_4$-alkoxy substituted $C_1$–$C_6$-alkyl, unsubstituted or halogen- or $C_1$–$C_4$-alkoxy substituted $C_2$–$C_7$-alkyl-carbonyl or unsubstituted or halogen- or $C_1$–$C_4$-alkoxy substituted $C_1$–$C_6$-alkylsulphonyl.

14. A compound according to claim 13, wherein
$R^3$ represents methyl,
$R^4$ represents hydrogen, and
$R^5$ represents fluorine.

* * * * *